United States Patent
Shuros et al.

(10) Patent No.: US 7,734,349 B2
(45) Date of Patent: Jun. 8, 2010

(54) OSMOMETRIC HEART MONITORING DEVICE AND METHODS

(75) Inventors: Allan Charles Shuros, St. Paul, MN (US); Eric A. Mokelke, White Bear Lake, MN (US); Michael John Kane, Lake Elmo, MN (US); Jihong Qu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 283 days.

(21) Appl. No.: 11/779,403

(22) Filed: Jul. 18, 2007

(65) Prior Publication Data

US 2009/0024177 A1    Jan. 22, 2009

(51) Int. Cl.
*A61B 5/14* (2006.01)

(52) U.S. Cl. .......................... 607/22; 600/508
(58) Field of Classification Search .................. 607/22
See application file for complete search history.

(56) References Cited

U.S. PATENT DOCUMENTS

| | | | |
|---|---|---|---|
| 5,040,533 A | 8/1991 | Fearnot | |
| 5,275,171 A | 1/1994 | Barcel | |
| 5,388,449 A | 2/1995 | LeVeen et al. | |
| 5,583,476 A | 12/1996 | Langford | |
| 6,224,550 B1 | 5/2001 | Ellingsen | |
| 6,237,398 B1 | 5/2001 | Porat et al. | |
| 6,268,161 B1* | 7/2001 | Han et al. | 435/14 |
| 6,692,528 B2 | 2/2004 | Ward et al. | |
| 6,915,149 B2 | 7/2005 | Ben-Haim | |
| 6,978,182 B2 | 12/2005 | Mazar et al. | |
| 7,356,366 B2* | 4/2008 | Sweeney et al. | 600/345 |
| 2005/0065556 A1 | 3/2005 | Reghabi et al. | |
| 2005/0070768 A1* | 3/2005 | Zhu et al. | 600/309 |
| 2005/0154272 A1* | 7/2005 | Dirac et al. | 600/365 |
| 2006/0173252 A1 | 8/2006 | Ellingsen et al. | |
| 2006/0241709 A1 | 10/2006 | Soykan et al. | |
| 2006/0287684 A1 | 12/2006 | Baynham et al. | |

FOREIGN PATENT DOCUMENTS

WO    WO-2007137037    11/2007

OTHER PUBLICATIONS

Han, In S. et al., "Constant-Volume Hydrogel Osmometer: A New Device Concept for Miniature Biosensors", *Biomacromolecules 2002, 3* 2002, pp. 1271-1275.

(Continued)

*Primary Examiner*—Carl H Layno
*Assistant Examiner*—Jeremiah T Kimball
(74) *Attorney, Agent, or Firm*—Pauly, DeVries Smith & Deffner, L.L.C.

(57) ABSTRACT

Embodiments of the invention are related to monitoring devices and methods with osmometric sensors, amongst other things. In an embodiment, the invention includes an implantable heart failure monitoring system including an osmometric sensor, the osmometric sensor configured to generate a signal corresponding to the osmotic strength of a bodily fluid, and a controller in communication with the osmometric sensor, the controller configured to receive and process the signal corresponding to the osmotic strength of a bodily fluid. Other aspects and embodiments are provided herein.

20 Claims, 11 Drawing Sheets

OTHER PUBLICATIONS

Kane, Michael J. et al., "U.S. Appl. No. 11/383,933", filed May 17, 2006.
Shotan, et al., "Fluid Overload Contributing to Heart Failure", *Nephrol Dial. Transplant* 2005, Suppl. 7:vii24-vii27.
Shuros, Allan C. et al., "U.S. Appl. No. 11/772,397", filed Jul. 2, 2007.
"International Search Report from International application No. PCT/US2008/069499".

* cited by examiner

OSMOMETRIC HEART MONITORING DEVICE AND METHODS

TECHNICAL FIELD

This disclosure relates generally to devices and methods for monitoring a patient's heart and, more particularly, to monitoring devices and methods with osmometric sensors, amongst other things.

BACKGROUND OF THE INVENTION

Diseases of the heart are a leading cause of death in the developed world. One exemplary disease of the heart is heart failure, afflicting over 5 million people in the United States, according to The National Heart Lung and Blood Institute (NHLBI). Heart failure refers to a clinical syndrome in which an abnormality of cardiac function causes a below normal cardiac output that can fall below a level adequate to meet the metabolic demand of peripheral tissues.

Ischemia is a condition that can be associated with many types of heart disease. Ischemia can be described as an inadequate flow of blood to a part of the body, caused by constriction or blockage of the blood vessels supplying it. Ischemia can be a very serious condition depending on what part of the body is receiving an inadequate flow of blood. For example, ischemia can result in myocardial infarction where parts of the myocardium fail to receive an adequate flow of blood because of a blockage or constriction in the coronary artery.

Monitoring patients' physiological state is an important aspect in the diagnosis, management and treatment of diseases and conditions of the heart, including heart failure and myocardial ischemia. As such, various monitoring systems have been developed over time. Many of these monitoring systems rely on sensing electrical activity of the heart and then evaluating this activity in order to determine the patient's physiological state. However, a need remains for additional types of monitoring systems that can provide accurate information about a patient's physiological state.

SUMMARY OF THE INVENTION

Embodiments of the invention are related to monitoring devices and methods with osmometric sensors, amongst other things. In an embodiment, the invention includes an implantable heart failure monitoring system including an osmometric sensor, the osmometric sensor configured to generate a signal corresponding to the osmotic strength of a bodily fluid, and a controller in communication with the osmometric sensor, the controller configured to receive and process the signal corresponding to the osmotic strength of a bodily fluid.

In an embodiment, the invention includes an implantable osmotic heart monitoring system including an osmotic pH sensor, the osmotic pH sensor configured to generate a signal corresponding to pH of a bodily fluid. The osmotic pH sensor can include a wall member defining an enclosed volume, the wall member including a semi-permeable membrane; and a solution including a solvent and a solute, the solution disposed within the enclosed volume, the solute configured to change osmotic strength in a pH range of between about 7.3 and about 7.5. The semi-permeable membrane can be permeable to the solvent and impermeable to the solute. The system can further include a controller in communication with the osmotic pH sensor.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Some diseases and conditions of the heart, such as heart failure, can be manifested through changes in the osmotic strength of extracellular fluid in the body. Normally, the renal system functions to maintain osmotic strength of bodily fluids within a desired normal range. However, in the context of heart failure, the characteristic reduced cardiac output has a depressing effect on renal function due to decreased renal perfusion, which causes a reduction in salt and water excretion by the pressure natriuresis mechanism. The renin-angiotensin-aldosterone system also promotes water and plasma volume retention to compensate for the reduced cardiac output. The increased sympathetic activity in response to low blood pressure and/or cardiac output may also depress renal function still further. As a result, the net effect of heart failure can include significant retention of fluid which may result in decreased osmotic strength of extracellular fluids in the body. For this reason, one approach to monitoring the condition and progress of heart failure patients is to monitor the osmotic strength of their extracellular fluids.

Embodiments of devices and systems included herein can include osmometric sensors allowing detection and monitoring of a patient's physiological state by measuring or estimating the osmotic strength of the patient's extracellular fluids. While not limiting the scope of that described herein, various aspects of exemplary embodiments will now be described in greater detail.

Figure 1:
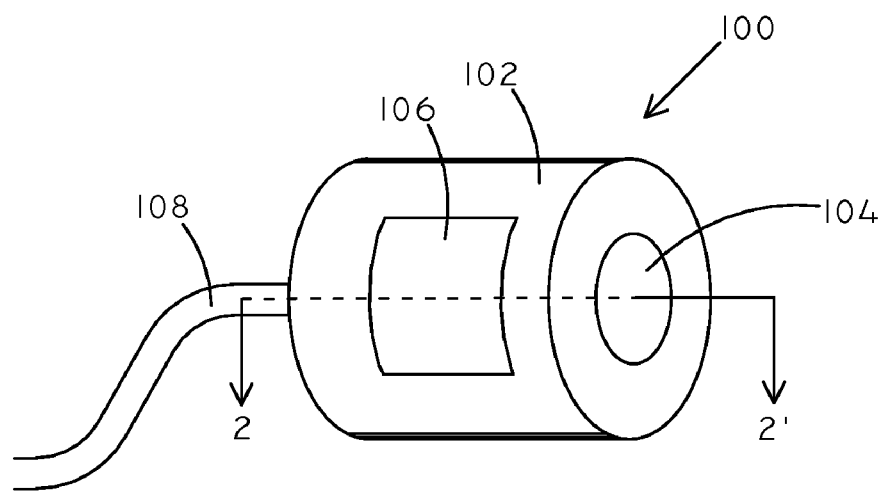
FIG. 1 is a schematic perspective view of an exemplary osmometric sensor in accordance with an embodiment of the invention.

Referring now to FIG. 1, a schematic perspective view is shown of an exemplary osmometric sensor 100 in accordance with an embodiment of the invention. The osmometric sensor 100 includes a wall member 102. The osmometric sensor 100 also includes a semi-permeable membrane 104. The wall member 102 can include various types of materials including polymers, metals, ceramics, and the like. The semi-permeable membrane can include materials such as those described below.

The osmometric sensor 100 also includes a signaling element 106. The signaling element 106 can include a component configured to generate a signal in response to flexion of the signaling element 106. The wall member 102 is attached to a lead member 108. The lead member 108 can include a lead body and a conductor and can serve to convey signals from the signaling element 106 to an implanted device (not shown).

Figure 2:
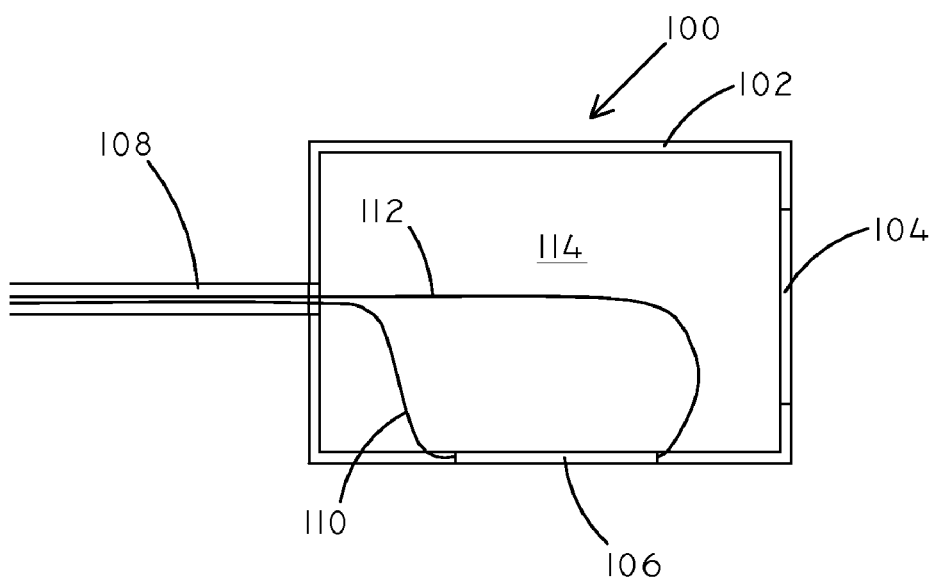
FIG. 2 is a schematic cross-sectional view of an exemplary osmometric sensor as taken along line 2-2' of FIG. 1.

Referring now to FIG. 2, a schematic cross-sectional view is shown of an exemplary osmometric sensor 100 as taken along line 2-2' of FIG. 1. The wall member 102, the semi-permeable membrane 104, and the signaling element 106 together define an interior volume 114. A solution including a solute and a solvent can be disposed within the interior volume 114.

In operation, pressure inside the enclosed volume 114 can change as a result of the process of osmosis. Osmosis is a physical process in which a solvent moves, without an additional input of energy, across a semi-permeable membrane (permeable to the solvent, but not a solute) separating two solutions having different osmotic strength. It will be appreciated that osmotic strength can be described and measured in terms of osmolarity and/or osmolality. The osmole (Osm) is a non-SI unit of measurement that defines the number of moles of osmotically active molecules in a solution. One osmole is equal to one mole of osmotically active molecules. Osmolarity is a measure of the osmoles per liter of solution. Osmolality is a measure of the osmoles per kilogram of solvent.

Net movement of solvent by osmosis is from the less-concentrated (hypotonic, lower osmotic strength) solution, to the more-concentrated (hypertonic, higher osmotic strength) solution. As such, where the solution within the enclosed volume 114 has a higher osmotic strength than the bodily fluid outside of the device, fluid can diffuse across the semi-permeable membrane 104 and into the enclosed volume 114, causing the pressure to increase therein. Conversely, where the solution within the enclosed volume 114 has a lower osmotic strength than the bodily fluid outside of the device, fluid can diffuse across the semi-permeable membrane 104 and out of the enclosed volume 114, causing the pressure therein to decrease.

In some embodiments, both the wall member 102 and the semi-permeable membrane are substantially rigid, resisting deformation. In some embodiments, the signaling element 106 is flexible. As such, changes in pressure inside of the enclosed volume 114 can result in flexion of the signaling element 106. Specifically, where the pressure inside of the enclosed volume 114 exceeds the pressure outside of the device, the signaling element 106 can flex outwardly, effectively expanding the enclosed volume 114. Conversely, where the pressure inside of the enclosed volume 114 is less than the pressure outside of the device, the signaling element 106 can flex inwardly, effectively shrinking the enclosed volume 114.

The signaling element 106 can be configured to generate a signal in response to flexion. By way of example, the signaling element 106 can be configured to generate an optical and/or an electrical signal in response to flexion. It will be appreciated that there are many ways of generating a signal based on flexion. As an example, the signaling element 106 can include a piezoelectric material, such as poly(vinylidene fluoride) (PVDF), that generates a current in response to flexion. As another example, the signaling element 106 can include a structure that changes its resistance in response to flexion. Exemplary resistance based flexion sensors are described in U.S. Pat. No. 5,583,476, the content of which is herein incorporated by reference. As another example, the signaling element 106 can include a structure wherein capacitance changes in response to flexion of the signaling element 106. In some embodiments, the signaling element 106 can include an optical fiber that is configured to detect flexion through signal loss.

A first conductor 110 and a second conductor 112 can provide signal communication with the signaling element 106. By way of example, in some embodiments, the first conductor 110 and the second conductor 112 can be electrical conductors and can provide electrical communication with the signaling element 106.

The signal produced by the signaling element 106 can be processed in order to derive osmotic strength in the bodily fluids surrounding the osmometric sensor. Specifically, the relationship between flexion and osmotic strength change can be determined and then applied in order to derive osmotic strength of a bodily fluid. In some embodiments, the relationship between flexion and osmotic strength can be pre-determined and programmed into the device. In some embodiments, the device can be calibrated using a series of solutions of known osmotic strength in order to adjust the relationship between flexion and osmotic strength.

Figure 3:
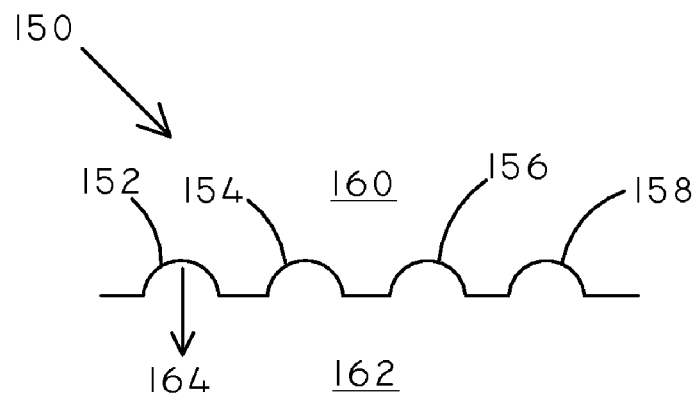
FIG. 3 is a schematic view of a transducing structure in accordance with an embodiment of the invention.

In some embodiments, the shape and configuration of signaling elements, or components thereof, can be configured to provide a non-linear response characteristic that improves the sensitivity of the device while maintaining a large dynamic range of operation above and below optimum physiological values. Referring now to FIG. 3, a transducing structure 150 is shown in accordance with an embodiment of the invention. The transducing structure 150 can be part of a signaling element of various embodiments described herein. The transducing structure 150 can include a plurality of dimples (152, 154, 156, 158) with a dome shape. The dimples (152, 154, 156, 158) can be configured to resist deformation until a threshold pressure differential exists between a first side 160 and a second side 162 of the transducing structure. For example, the dimples can be made of a semi-rigid material. Once a threshold pressure differential has been reached, the dimples can flex outwardly (invert) in the direction of arrow 164. The dimples can include a material, such as a piezoelectric material or a material that changes resistance based on flexion, so that a detectable signal can be generated when the dimples invert. In some embodiments, each of the dimples can be configured to invert at a different threshold pressure differential. In this manner, changes in osmotic strength, as manifested by changes in pressure, can be detected by a signaling element in a non-linear manner. It will be appreciated that other structures to produce a non-linear response characteristic are also contemplated herein.

As described above, the enclosed volume can include a solvent and one or more solutes. In some embodiments, the solvent is water. The solute can include many different types of chemical compounds. By way of example, the solute can include a protein, a carbohydrate, inorganic or organic salts, inorganic or organic acids or bases, lipids, amino acids, and the like. In an embodiment, the solute includes a biocompatible chemical compound. In an embodiment, the solute includes a chemical compound naturally occurring within the body. In an embodiment, the solute includes medium to low molecular weight compounds with high stability and low toxicity. In an embodiment, the solute includes one or more of sodium chloride, calcium chloride, magnesium chloride, potassium chloride, and manganese chloride. In an embodiment, the solute includes one or more phosphates (such as calcium phosphate) and/or carbonates (such as calcium carbonate). In an embodiment, the solute is glucose. In an embodiment, the solute is albumen. Further examples of solutes are described below.

A normal value of osmotic strength in fluids of the body is between about 280 and 303 mOsm per kg. As such, in some embodiments, the solution within the enclosed volume 114 has a starting osmotic strength of between about 280 and 303 mOsm per kg when the device is implanted within a patient.

Figure 4:
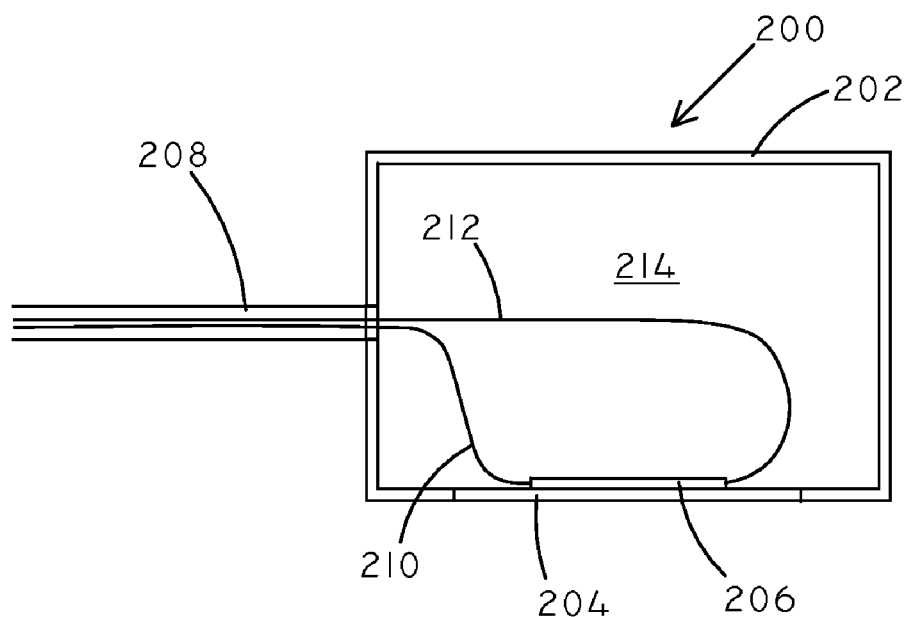
FIG. 4 is a schematic cross-sectional view of an osmometric sensor in accordance with another embodiment of the invention.

In some embodiments, the signaling element and the semi-permeable membrane can be disposed adjacent to one another. Referring now to FIG. 4, a schematic cross-sectional view is shown of an osmometric sensor 200 in accordance with another embodiment. The osmometric sensor 200 includes wall member 202, a semi-permeable membrane 204, and a signaling element 206 disposed over the semi-permeable membrane 204. In this embodiment, the wall member 202 is substantially rigid, but both the semi-permeable membrane 204 and the signaling element 206 are flexible. As the pressure inside the enclosed volume 214 changes due to osmosis, the semi-permeable membrane 204 and the signaling element 206 can flex, with the signaling element 206 generating a signal. One or more conductors, such as first conductor 210 and second conductor 212, can pass through a lead 208 in order to provide communication with the signaling element 206.

Figure 5:
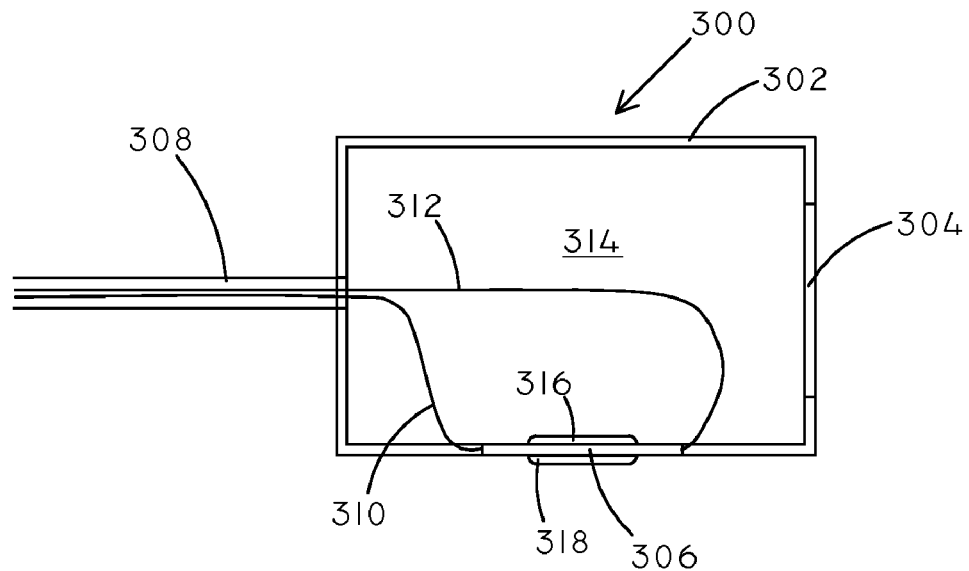
FIG. 5 is a schematic cross-sectional view of an osmometric sensor in accordance with another embodiment of the invention.

In some embodiments, the osmometric sensor can include one or more sensors that sense pressure, and then the osmotic strength of bodily fluid outside of the osmometric sensor can be calculated based on the sensed pressures. By way of example, referring now to FIG. 5, an osmometric sensor 300 is shown in accordance with another embodiment of the invention. The osmometric sensor 300 includes a wall member 302, a semi-permeable membrane 304, and a signaling element 306. The wall member 302, the semi-permeable membrane 304, and the signaling element 306 can define an enclosed volume 314. The wall member 302, the semi-permeable membrane 304, and the signaling element 306 can all be made of rigid materials so that the enclosed volume 314 does not change in size significantly. One or more conductors, such as first conductor 310 and second conductor 312, can pass through a lead 308 in order to provide communication with the signaling element 306.

The signaling element 306 can include a first pressure sensor 316 and a second pressure sensor 318. The first and second pressure sensors 316, 318 can include any type of pressure sensor, for example an electrical, mechanical, or optical pressure sensor. By way of example, some exemplary pressure sensors are described in U.S. Pat. No. 6,237,398, the content of which is herein incorporated by reference. The first pressure sensor 316 can be configured to produce a signal corresponding to the pressure inside of the enclosed volume 314. The second pressure sensor 318 can be configured to produce a signal corresponding to the pressure outside of the enclosed volume 314. The difference between the pressure inside of the enclosed volume 314 and outside of the enclosed volume is due to the process of osmosis. This difference can be directly measured by subtracting the pressure as measured by second pressure sensor 318 from the pressure as measured by first pressure sensor 316. This measured difference can then be used to determine the difference in osmotic strength between the solution inside of the enclosed volume and the extracellular fluid. Using the difference in osmotic strength, where the osmotic strength of the solution inside of the enclosed volume is known, the osmotic strength of the extracellular fluid can then be calculated.

Figure 6:
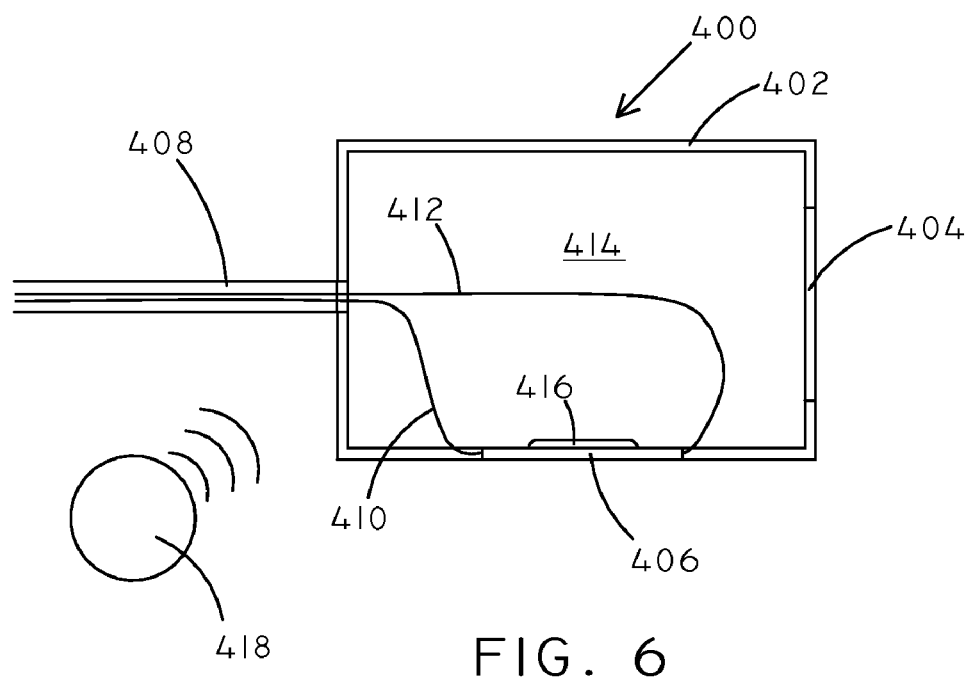
FIG. 6 is a schematic cross-sectional view of an osmometric sensor in accordance with another embodiment of the invention.

It will be appreciated that the local (or ambient) pressure inside of a patient, as used in embodiments herein, can also be measured by a pressure sensor that is physically detached from the osmometric sensor. By way of example, the local pressure inside of a patient can be measured by a remote (or satellite) sensor that is in wireless communication with other components of a system or device as described herein. Referring now to FIG. 6, an osmometric sensor 400 is shown in accordance with another embodiment of the invention. The osmometric sensor 400 includes a wall member 402, a semi-permeable membrane 404, and a signaling element 406. The wall member 402, the semi-permeable membrane 404, and the signaling element 406 can define an enclosed volume 414. One or more conductors, such as first conductor 410 and second conductor 412, can pass through a lead 408 in order to provide communication with the signaling element 406.

The signaling element 406 can include a first pressure sensor 416. The first pressure sensor 416 can be configured to produce a signal corresponding to the pressure inside of the enclosed volume 414. A second pressure sensor 418 can be disposed remotely from the first pressure sensor 416. The second pressure sensor 418 can be configured to produce a signal corresponding to the pressure outside of the enclosed volume 414. The second pressure sensor 418 can be configured to generate a signal that can be transmitted wirelessly to other components of a system including the osmometric sensor. By way of example, the second pressure sensor 418 can be configured to transmit a signal via radiofrequency (RF), acoustically, inductance, optically, or the like.

Figure 7:
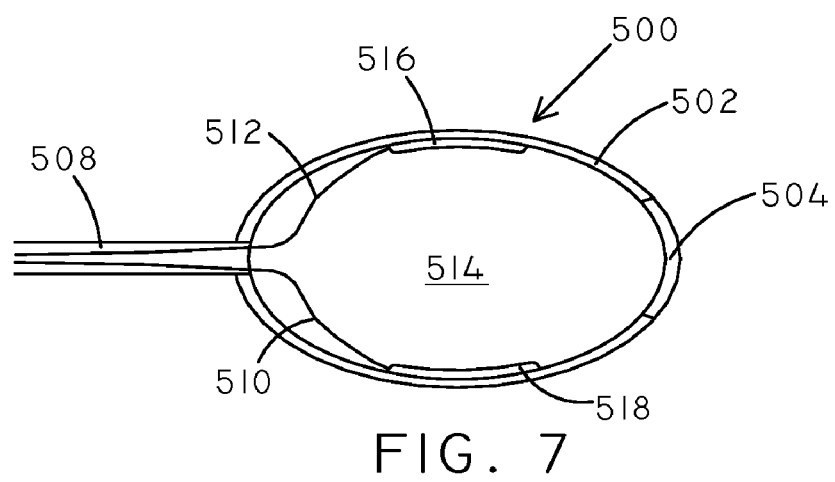
FIG. 7 is a schematic cross-sectional view of an osmometric sensor in accordance with another embodiment of the invention.

In some embodiments, the osmometric sensor can use an impedance measurement in order to derive osmotic strength. In some embodiments, an impedance based osmometric sensor can include an enclosed volume that is configured to expand and contract in response to changes in osmotic strength of an enclosed volume. Referring now to FIG. 7, a schematic cross-sectional view of an osmometric sensor 500 is shown in accordance with another embodiment. The osmometric sensor 500 includes a wall member 502 and a semi-permeable membrane 504. The wall member 502 and the semi-permeable membrane 504 together can define an enclosed volume 514. A solution including one or more solutes and a solvent can be disposed within the enclosed volume. A first electrode 516 and a second electrode 518 can be disposed against the wall member 502. In some embodiments, the first electrode 516 and the second electrode 518 are disposed on opposite sides of the wall member 502, within the enclosed volume 514.

The wall member 502 and/or the semi-permeable membrane 504 can be elastic such that the enclosed volume 514 can change in size as water passes into or out of the enclosed volume due to osmosis. The total amount of the solute within the enclosed volume can be fixed, however, as water passes into or out of the enclosed volume, the concentration of the solute within the enclosed volume changes. The solute can include a species that contributes to impedance through the enclosed volume based on its concentration. Therefore, impedance will vary as the enclosed volume increases or decreases as a result of changes in osmotic strength of bodily fluids surrounding the osmometric sensor. Impedance can be measured between the first electrode 516 and the second electrode 518. After impedance is measured, in one embodiment, osmotic strength can be derived according to a lookup table mapping specific impedance values to specific osmotic strength values. Such a lookup table can be calibrated before or after implant of the device (in vitro or in vivo calibration). First conductor 510 and second conductor 512 can pass through a lead 508 and connect to second electrode 518 and first electrode 516 respectively in order to provide electrical communication.

Figure 8:
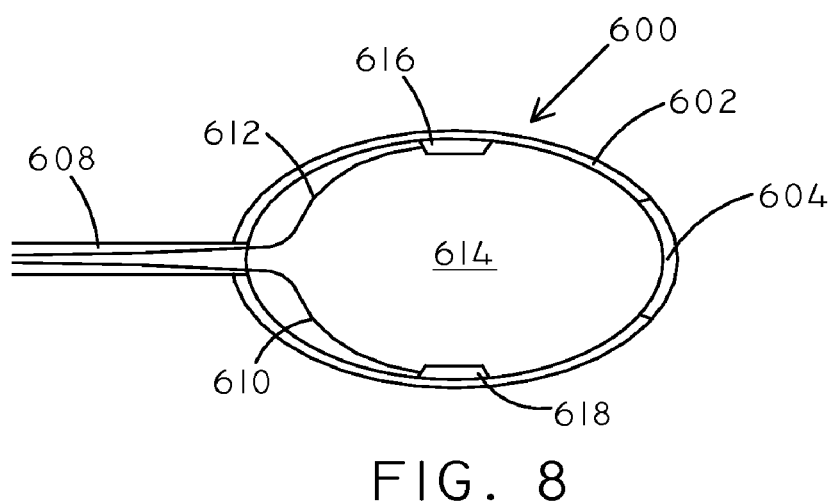
FIG. 8 is a schematic cross-sectional view of an osmometric sensor in accordance with another embodiment of the invention.

In some embodiments, the osmometric sensor can use an optical measurement in order to derive osmotic strength. Referring now to FIG. 8, a schematic cross-sectional view of an osmometric sensor 600 is shown in accordance with another embodiment. The osmometric sensor 600 includes a wall member 602 and a semi-permeable membrane 604. The wall member 602 and the semi-permeable membrane 604 together can define an enclosed volume 614. An optical excitation assembly 616 and an optical detection assembly 618 can be disposed against the wall member 602. In some embodiments, the optical excitation assembly 616 and the optical detection assembly 618 are disposed on opposite sides of the wall member 602, within the enclosed volume 614.

The wall member 602 and/or the semi-permeable membrane 604 can be elastic such that the enclosed volume 614 can change in size. Specifically, the wall member 602 and or the semi-permeable membrane 604 can be configured so that the distance between the optical excitation assembly 616 and the optical detection assembly 618 can increase as the enclosed volume expands. Signal loss of electromagnetic energy (such as light) can be measured between the optical excitation assembly 616 and the optical detection assembly 618. For example, light can be emitted from the optical excitation assembly 616 and then received by the optical detection assembly 618. The farther light passes through the enclosed volume 614, the more light will be lost to diffusion. To enhance losses of optical signal intensity between the excitation assembly 616 and the detection assembly 618, in some embodiments, the enclosed volume 614 can be filled with a solution containing a component that enhances diffusion and/or absorbs light.

The optical excitation assembly 616 can include a light source, such as a light emitting diode (LED). The optical detection assembly 618 can include a light receiver, such as a charge-coupled device (CCD), photodiode, a junction field effect transistor (JFET) type optical sensor, or a complementary metal-oxide semiconductor (CMOS) type optical sensor.

The strength of the optical signal, as detected by the optical detection assembly 618 can then be used to assess the osmotic strength of the bodily fluid which surrounds the osmotic device. The greater the signal loss, the larger the distance between the optical excitation assembly 616 and the optical detection assembly 618, and therefore the lower the osmotic strength of the bodily fluid. This relationship exists because the lower the osmotic strength in the bodily fluid, the more fluid will pass from bodily fluid and into the enclosed volume 614, thereby expanding the size of the enclosed volume 614.

In another embodiment, the osmometric sensor can directly measure the concentrations of various physiological solutes in order to estimate osmotic strength. For example, osmotic strength in plasma can be estimated according to the following formula:

$$\text{Plasma Osmolality(mOsm/kg)} \approx 2([Na^+]+[K^+]) + ([BUN]/2.8) + ([Glucose]/18)$$

wherein $[Na^+]$ is moles of sodium ion per kg of solvent, $[K^+]$ is moles of potassium ion per kg of solvent, [BUN] is milligrams of blood urea nitrogen per deciliter of solvent, and [Glucose] is milligrams of glucose per deciliter of solvent. As such in an embodiment, the osmotic sensor can include a chemical sensor to determine the concentrations of one or more physiological solutes such as sodium ion, potassium ion, glucose, and blood urea nitrogen. Many different types of chemical sensors can be used including potentiometric, calorimetric, and fluorimetric chemical sensors. One example of a suitable chemical sensor is described in U.S. patent application Ser. No. 11/383,933, the content of which is herein incorporated by reference.

Figure 9:
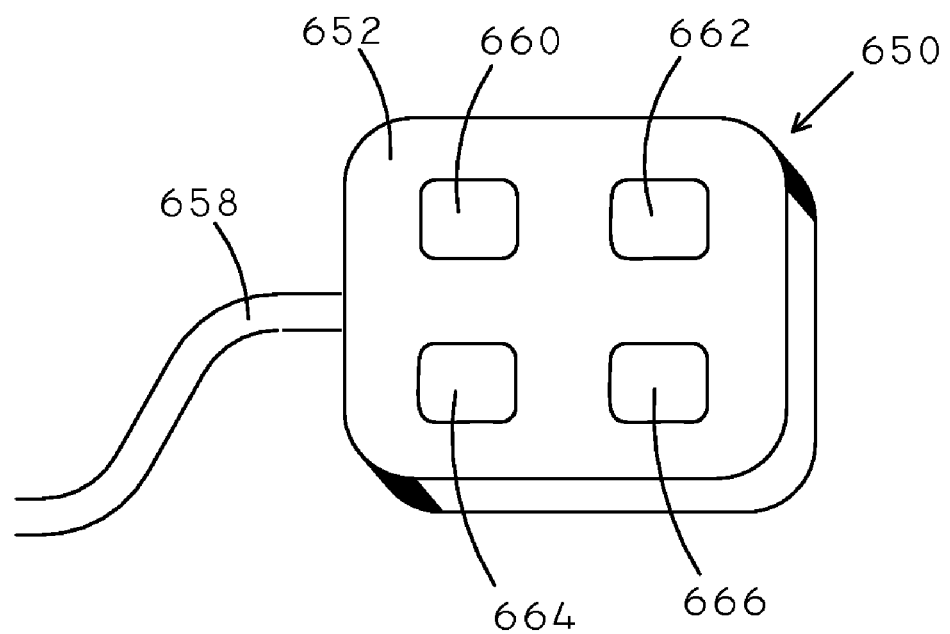
FIG. 9 is a schematic perspective view of an osmometric sensor in accordance with another embodiment of the invention.

Referring now to FIG. 9, a schematic perspective view of an osmometric sensor is shown in accordance with another embodiment of the invention. The osmometric sensor 650 includes a lead member 658 and a chemical sensor array 652. The osmometric sensor 650 can include a plurality of chemical sensing elements 660, 662, 664, and 666. In some embodiments, each of the chemical sensing elements 660, 662, 664, and 666 can be configured to detect the concentration of a different physiological solute. For example, in some embodiments, chemical sensing element 660 can be configured to measure the concentration of sodium ion. In some embodiments, chemical sensing element 662 can be configured to measure the concentration of potassium ion. In some embodiments, chemical sensing element 664 can be configured to measure the concentration of blood urea nitrogen (BUN). In some embodiments, chemical sensing element 666 can be configured to measure the concentration of glucose.

Many other types of osmometric sensors can also be used. One example of an osmometric sensor is described in U.S. Pat. No. 5,388,449, the content of which is herein incorporated by reference.

It will be appreciated that osmometric sensors as described herein can be implanted into a subject in many different locations. In some embodiments, the osmometric sensor can be implanted intravascularly. By way of example, the osmometric sensor can be disposed within the subclavian vein, the superior or inferior vena cava, the right or left atrium, the right or left ventricle, the pulmonary artery, the coronary sinus, and the like. In other embodiments, the osmometric sensor can be implanted extravascularly. By way of example, the osmometric sensor can be implanted pericardially, in the peritoneal cavity, in the interpleural space, in the lungs, etc. In some embodiments, the osmometric sensor can be implanted within the renal system. In some embodiments, the osmometric sensor can be implanted within domains containing interstitial fluid, lymph fluid, cerebrospinal fluid, and the like.

Figure 10:
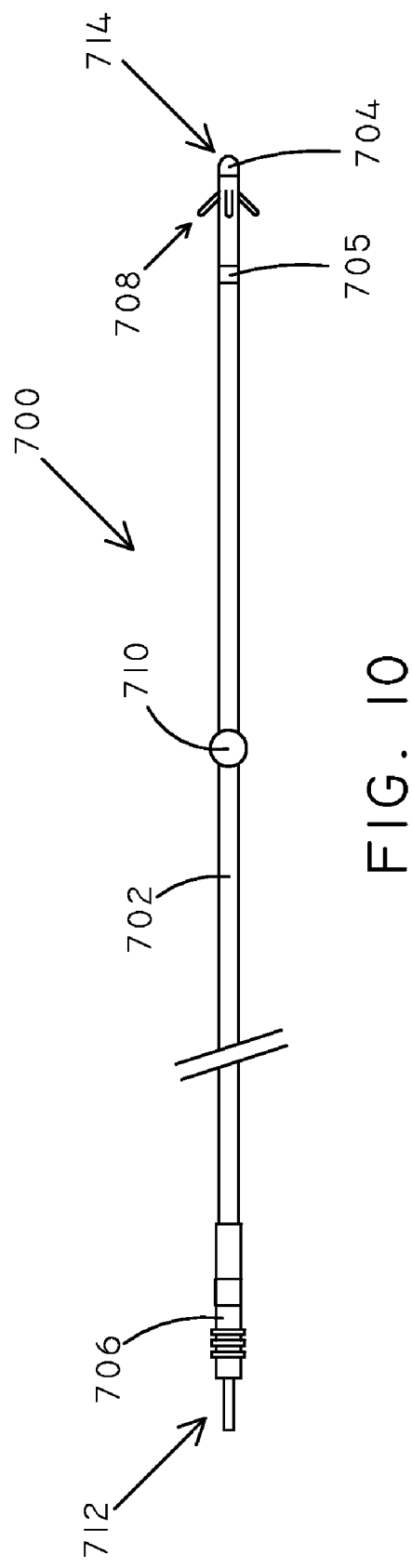
FIG. 10 is a schematic view of an electrical stimulation lead in accordance with an embodiment of the invention.

In some embodiments, osmometric sensors as described herein can be part of other implantable devices or systems. For example, in some embodiments, an osmometric sensor can be coupled to a lead, such as an electrical stimulation lead. Referring now to FIG. 10, a schematic view of an electrical stimulation lead 700 is shown in accordance with an embodiment of the invention. The electrical stimulation lead 700 includes a lead body 702 with a proximal end 712 and a distal end 714. The electrical stimulation lead 700 includes a first stimulation electrode 704 and a second stimulation electrode 705 positioned near the distal end 714. In some embodiments, the first stimulation electrode 704 can be referred to as a tip electrode and the second stimulation electrode 705 can be referred to as a ring electrode. The electrical stimulation lead 700 can include one or more conductors (not shown) disposed within the lead body 702. It will be appreciated that the stimulation lead 700 can be a pacing lead, defibrillating lead, a coronary venous lead, or the like. In some embodiments, such as where the stimulation lead is to be used for defibrillation in addition to pacing, the stimulation lead can also include a shocking coil near the distal end 714 of the stimulation lead.

The stimulation lead 700 further includes a connection plug 706 for connecting the stimulation lead 700 to an implantable device, such as a cardiac rhythm management (CRM) device. The connection plug 706 can be compatible with various standards for lead-header interface design including the DF-1, VS-1, IS-1 and IS-4 standards. The connection plug 706 can include multiple electrical contacts corresponding to different conductors disposed within the stimulation lead. In some embodiments, the stimulation lead can include a fixation element 708 in order to aid in engaging the stimulation lead with target tissue for stimulation, such as cardiac tissue.

An osmometric sensor 710 can be disposed on the lead body 702. The osmometric sensor 710 can be configured to generate a signal that is correlated to the osmotic strength of bodily fluids in the area of the osmometric sensor 710. In an embodiment, the osmometric sensor 710 can be coupled to the lead body at a point closer to the distal end 714 of the stimulation lead than the proximal end 712 of the stimulation lead 700. In other embodiments, the osmometric sensor 710 can be coupled to the lead body at a point closer to the proximal end 712 of the stimulation lead 700 than the distal end 714 of the stimulation lead 700.

Figure 11:
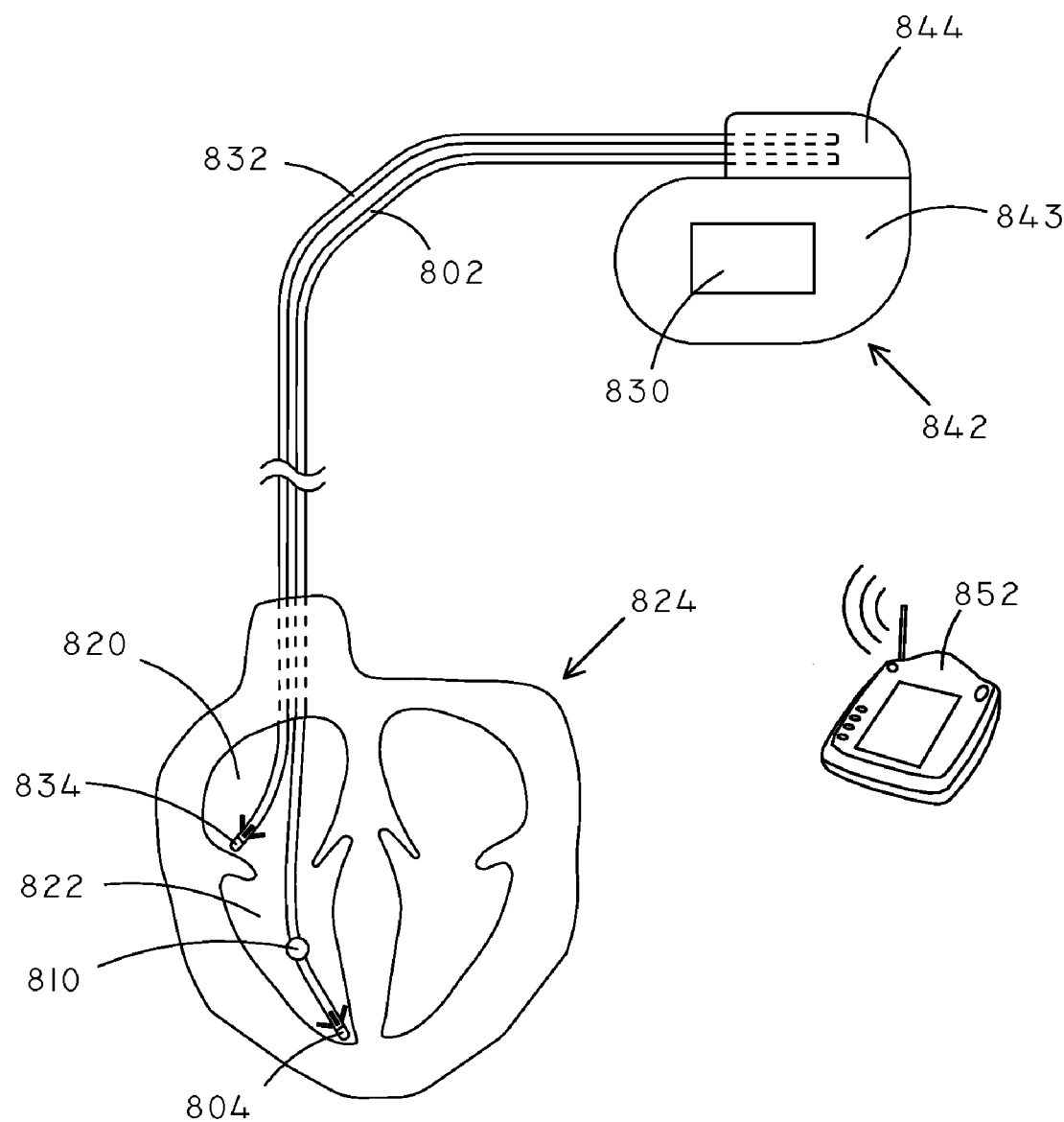
FIG. 11 is a schematic view of a monitoring device in conjunction with an osmometric sensor in accordance with an embodiment of the invention.

In some embodiments, signals from the osmometric sensor can pass through a lead member, or a stimulation lead, to a monitoring device. In some embodiments, the monitoring device can be a cardiac rhythm management (CRM) device. Referring now to FIG. 11 a schematic view of a monitoring device 842 in conjunction with an osmometric sensor 810 is shown in accordance with an embodiment of the invention. The monitoring device 842 can include a housing 843 and a header assembly 844. The monitoring device 842 can also include a controller module 830. The monitoring device 842 can be coupled to one or more leads 802, 832. The leads 802, 832 can include electrodes 804 and 834, respectively. In specific, the monitoring device 842 can be coupled to a lead 802 that is coupled to an osmometric sensor 810. However, it will be appreciated that in some embodiments, the monitoring device 842 and the osmometric sensor 810 can be in wireless communication.

In the view shown in FIG. 11, the electrodes 804 and 834 are positioned within the right ventricle 822 and right atrium 820, respectively, of the heart 824. Based on the relative positioning of the osmometric sensor 810 on lead 802, the osmometric sensor 810 is positioned within the right ventricle 822 of the heart 824 in this view. However, it will be appreciated that an osmometric sensor can be disposed within other areas of the body as well. For example, in some embodiments, an osmometric sensor can be positioned on a lead passing into the coronary venous system so that the osmometric sensor itself is positioned within the coronary venous system. While not intending to be bound by theory, positioning of the osmometric sensor within the coronary venous system, such as on a coronary venous lead, can be desirable because of the sensitivity and/or specificity allowed for by measuring osmotic strength of cardiac plasma within the coronary venous system.

In some embodiments, an osmometric sensor can be positioned so that it is disposed outside of the heart 824. For example, an osmometric sensor can be disposed on a lead in a position so that the osmometric sensor is disposed within the subclavian vein, or another portion of the vasculature between the subclavian vein and the heart.

An external monitoring device 852 can also be included with embodiments herein and can be in wireless communication with the monitoring device 842. For example, data regarding the osmometric sensor, as stored by the controller 830, can be wirelessly transmitted to the external monitoring device 852. The external monitoring device 852 can be a bedside monitoring system, an external programmer, and/or a patient management system. An exemplary patient management system includes the LATITUDE® patient management system, commercially available from Boston Scientific Corporation, Natick, Mass. Aspects of an exemplary patient management system are described in U.S. Pat. No. 6,978,182, the contents of which are herein incorporated by reference.

Figure 12:
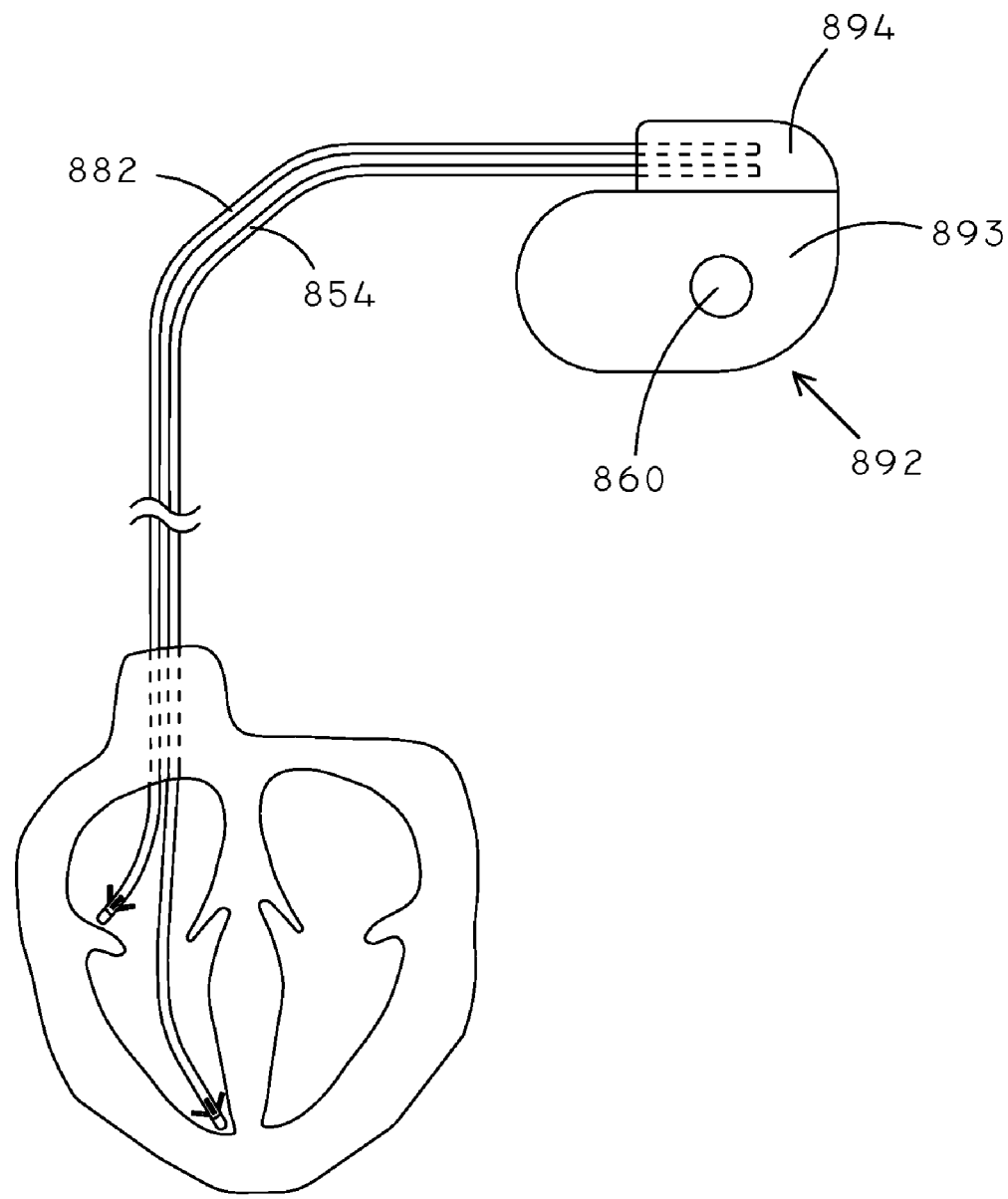
FIG. 12 is a schematic view of a monitoring device in conjunction with an osmometric sensor in accordance with an embodiment of the invention.

In some embodiments, the osmometric sensor can be coupled to the housing of a monitoring device and/or a CRM device. Referring now to FIG. 12 a schematic view of a monitoring device 892 in conjunction with an osmometric sensor 860 is shown in accordance with an embodiment of the invention. The monitoring device 892 can include a housing 893 and a header assembly 894. The monitoring device 892 can be coupled to one or more leads 854, 882. An osmometric sensor 860 can be disposed on the housing 893 of the monitoring device 892. In some embodiments, an osmometric sensor can be disposed on the header assembly.

Figure 13:
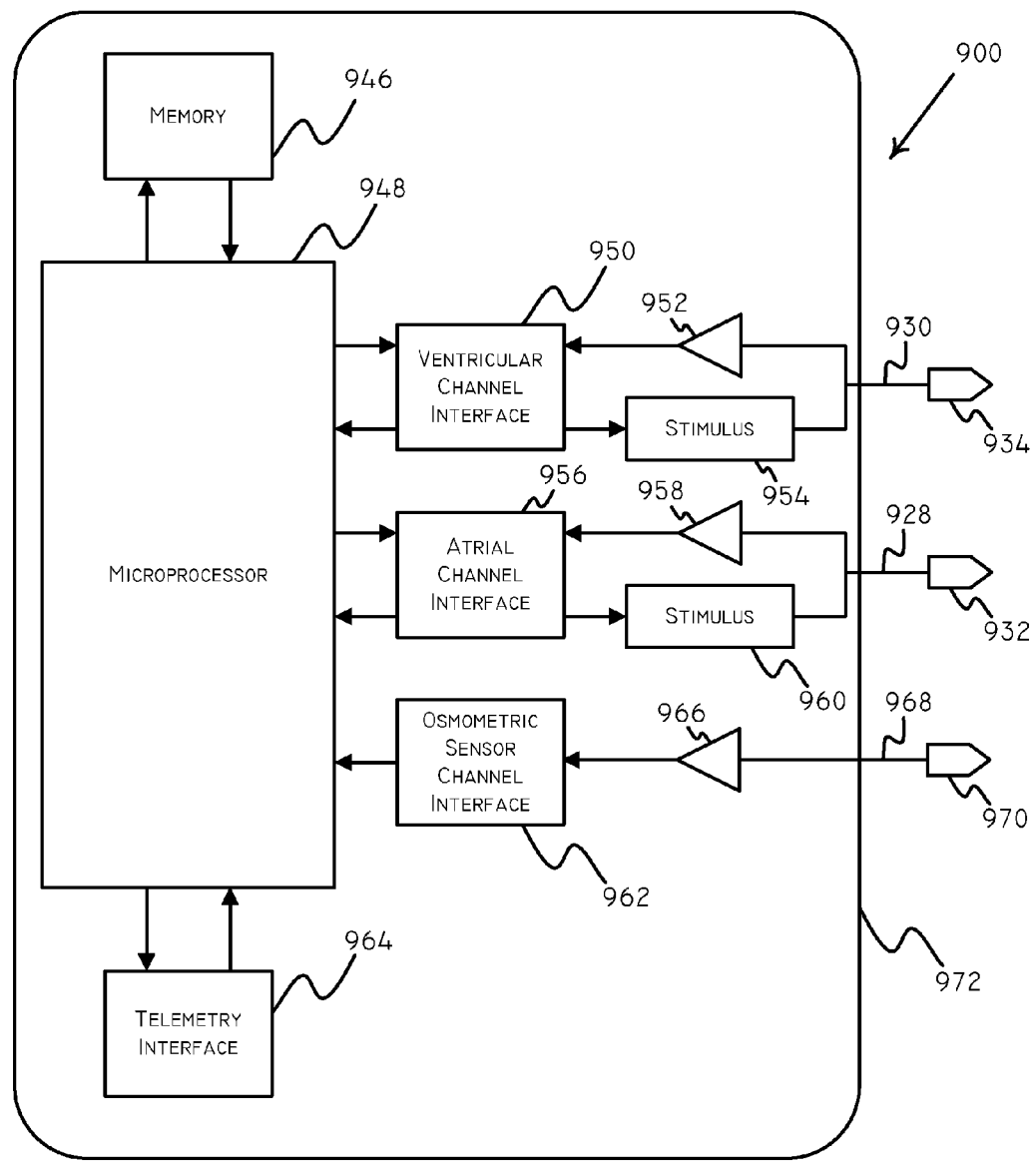
FIG. 13 is a schematic view of some components of an exemplary implantable system in accordance with an embodiment of the invention.

Embodiments of the invention can specifically include implantable systems including an implantable medical device, such as a CRM device, along with one or more electrical stimulation leads, and one or more osmometric sensors. Implantable medical devices can specifically include pacemakers, implantable cardioverter-defibrillators (ICDs), cardiac resynchronization therapy (CRT) devices, and the like. Implantable medical devices can include various components in order to receive and process signals from osmometric sensors. Referring now to FIG. 13, some components of an exemplary implantable system 900 are schematically illustrated. The implantable medical system 900 can include a controller module 972 coupled to one or more stimulation leads 930 and 928. The controller module 972 can also be coupled to an osmometric sensor 970 via a conductor 968 that can provide communication between the osmometric sensor 970 and the controller module 972.

The controller module 972 can include a microprocessor 948 (or processor) that communicates with a memory 946 via a bidirectional data bus. The memory 946 typically includes ROM or RAM for program storage and RAM for data storage. The controller module 972 can be configured to execute various operations such as processing of signals and execution of methods as described herein. A telemetry interface 964 is also provided for communicating with an external unit, such as a programmer device or a patient management system.

The controller module 972 can include ventricular sensing and pacing channels including sensing amplifier 952, output circuit 954, and a ventricular channel interface 950 which communicates bidirectionally with a port of microprocessor 948. The ventricular sensing and pacing channel can be in communication with stimulation lead 930 and electrode 934. The controller module 972 can include atrial sensing and pacing channels including sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

The controller module 972 can also include an osmometric sensor channel including sensing amplifier 966 and an osmometric sensor channel interface 962 which communicates with a port of microprocessor 948. The osmometric sensor channel can be in communication with osmometric sensor 970 via conductor 968. In some embodiments, conductor 968 is disposed within a stimulation lead, such as stimulation lead 928 or 930.

Implantable systems with osmometric sensors as described herein can be configured to execute various operations and/or methods. For example, a controller module can be configured to process a signal corresponding to the osmotic strength of a bodily fluid. Processing of a signal can include various operations such as converting the signal into information regarding osmotic strength, storing information regarding the signal, evaluating the osmotic strength in relation to various thresholds, and the like.

Figure 14:
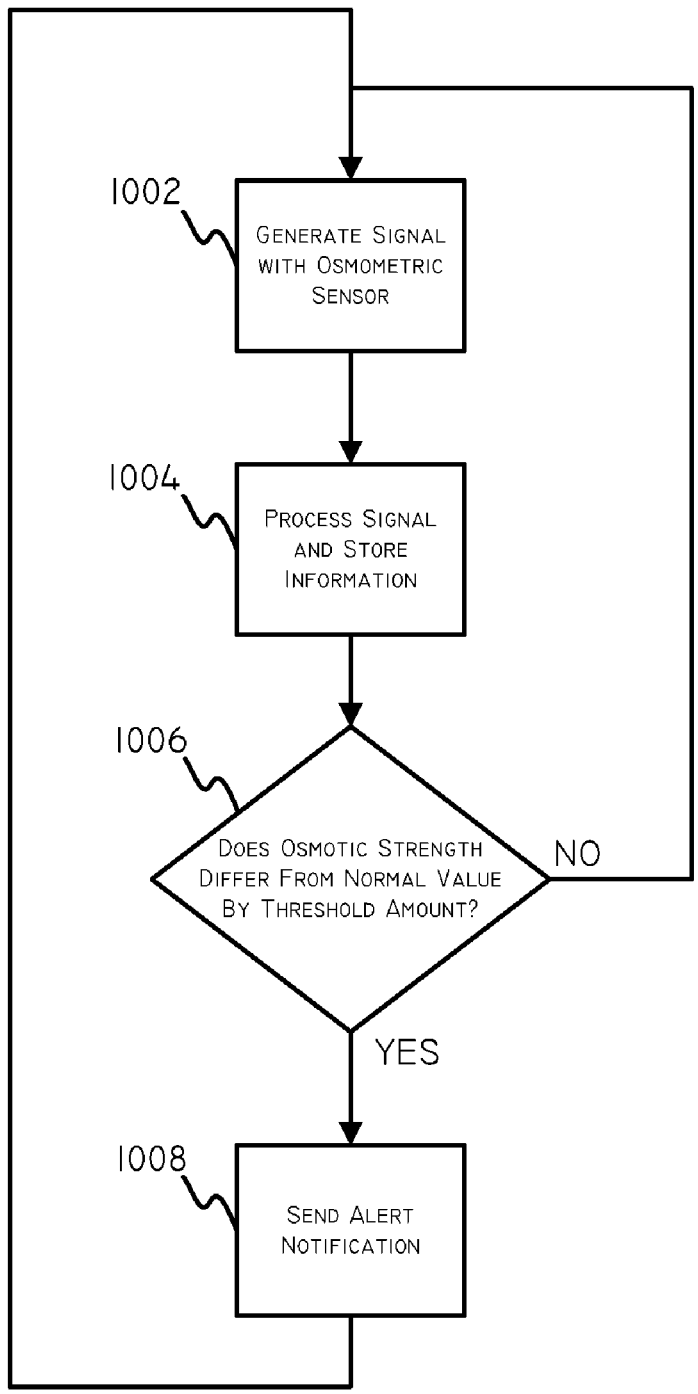
FIG. 14 is a flow chart of an exemplary method in accordance with an embodiment of the invention.

Referring now to FIG. 14, an exemplary method is shown in accordance with an embodiment of the invention. In a first operation 1002, an implantable system generates a signal regarding the osmotic strength of a bodily fluid using an osmometric sensor. In a second operation 1004, the system can process the signal to determine the osmotic strength of the bodily fluid and store information regarding the same. In a third operation 1006, the system can evaluate whether or not the osmotic strength of the bodily fluid differs from a normal physiological range by a threshold value. The threshold value can be programmed into the system by a care provider. If the threshold value is exceeded, then in a fourth operation 1008, the system can send an alert notification to a care provider though an external device. However, if the threshold value is not exceeded, then the system can repeat the method starting with the first operation 1002.

In some embodiments, the invention can include an implantable system configured to initiate or modulate therapy in response to changes in osmotic strength of a bodily fluid as detected with an osmometric sensor. In general, lower than normal osmotic strength of bodily fluids is associated with increased plasma volume because of fluid retention. One approach to treating this condition is to reduce plasma volume, traditionally accomplished through the administration of diuretic active agents. It is believed that increasing a patient's pacing rate can result in increased glomerular filtration and, therefore, decreased plasma volume. As such, in some embodiments, the system can be configured to modulate a cardiac pacing rate based on a signal generated by the osmometric sensor. In some embodiments, the minimum pacing rate of a monitoring and/or pacing device implanted in a patient, such as a pacemaker, can be increased if below normal osmotic strength is detected.

Figure 15:
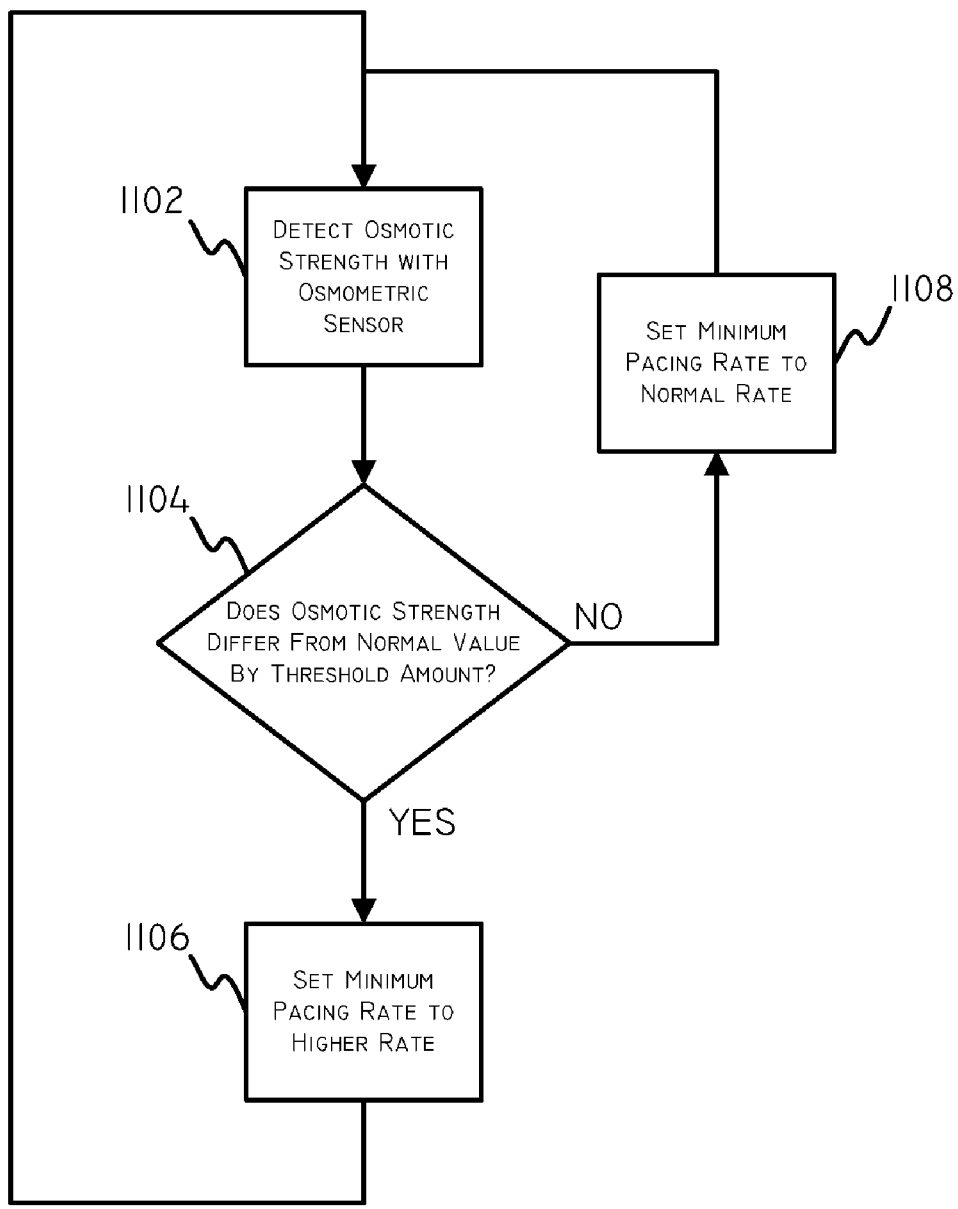
FIG. 15 is a flow chart of an exemplary method in accordance with an embodiment of the invention.

Referring now to FIG. 15, an exemplary method is shown in accordance with another embodiment of the invention. In a first operation 1102, osmotic strength can be detected with an osmometric sensor. In a second operation 1104, the osmotic strength can be evaluated in comparison to normal values (normal based on historical values or based on a programmed setting). If the measured osmotic strength is less than a normal value by at least a threshold amount, then in operation 1106, the pacing rate of a pacing device can be increased, such as the minimum pacing rate. In some embodiments, the minimum pacing rate can be increased by a certain fixed amount. In other embodiments, the minimum pacing rate can be increased by an amount proportional to the difference between the measured osmotic strength and a normal osmotic strength value. However, if the measured osmotic strength does not differ from a normal value by at least a threshold amount, then in operation 1108, the minimum pacing rate can be set to a normal minimum pacing rate. Embodiments of the invention can include implantable medical devices configured to execute these operations.

It will be appreciated that in various embodiments other therapeutic steps can be initiated by a device in order to counteract the increased plasma volume frequently associated with below normal osmotic strength of bodily fluids. By way of example, in some embodiments, stimulation can be applied to the vagus nerve. In some embodiments, diuretic therapy with an active agent can be initiated, such as through activation of a drug pump or by providing a prompt to a patient to take a diuretic medication.

Osmotic pH Sensors and Related Systems

Myocardial ischemia is a serious condition affecting the heart. Generally, however, acute myocardial ischemia does not result in significant changes in osmotic strength of extracellular fluids. However, ischemia does result in changes in pH of extracellular fluids. Specifically, ischemia results in decreased pH in those tissues where perfusion is insufficient. Increased concentrations of dissolved $CO_2$ and increased concentrations of lactic acid are believed to contribute to this decrease in pH.

Where an osmometric sensor includes a solute that changes its chemical form in response to changes in pH, such changes in pH in the extracellular fluid can be manifested by changes in osmotic pressure within an enclosed volume of an osmometric sensor. As such, embodiments of devices and systems included herein can include osmotic pH sensors allowing detection and monitoring of a patient's physiological state by measuring or estimating the pH of the patient's extracellular fluids.

As described above, embodiments of osmometric sensors described herein can include osmotic pH sensors. Such osmotic pH sensors can be used for the detection of conditions such as ischemia that result in a change in pH, but not necessarily a change in extracellular fluid osmotic strength. The following diagram shows a generalized chemical reaction that can occur when the pH changes, such as in the context of the dissociation of an acid.

Because osmotic strength is a coligative property, it is affected by compounds dissociating into subcomponents (or osmotically active species). By way of example, a solution composed entirely of dissociated $H^+$ and $A^-$ would have twice the osmotic strength of a solution where the solute is entirely in the form of HA. As such, osmometric sensors as described herein can function as osmotic pH sensors if the volume enclosed by the osmometric sensor includes a solute that can dissociate/associate in response to pH changes within the possible range of physiological pH values. For example, the enclosed volume of an osmometric sensor (such as that shown in FIGS. 1-2 and 4-8) can include a solute with a pKa between about 6.0 and about 10.0. Generally, a compound is 50% dissociated when pH is equal to a compound's pKa value. Such a solute will thus cause an effect on the osmotic strength of the solution within the enclosed volume when the pH changes within the possible range of physiological pH values.

Many different solutes can be used in osmotic pH sensors of the invention. By way of example, exemplary solutes can include 2-(N-Morpholino)ethanesulfonic acid (pKa=6.1); Bis(2-hydroxyethyl)iminotris(hydroxymethyl)methane (pKa=6.5); N-(2-Acetamido)-2-iminodiacetic acid (pKa=6.6); 2-[(2-Amino-2-oxoethyl)amino]ethanesulfonic acid (pKa=6.8); Piperazine-N,N'-bis(2-ethanesulfonic acid) (pKa=6.8); 3-(N-Morpholino)-2-hydroxypropanesulfonic acid (pKa=6.9); 1,3-Bis[tris(hydroxymethyl)methylamino] propane (pKa=6.8); N,N-Bis(2-hydroxyethyl)-2-aminoethanesulfonic acid (pKa=7.1); 3-(N-Morpholino)propanesulfonic acid (pKa=7.2); N-(2-Hydroxyethyl)piperazine-N'-(2-ethanesulfonic acid) (pKa=7.5); N-Tris(hydroxymethyl) methyl-2-aminoethanesulfonic acid (pKa=7.5); 3-[N,N-Bis (2-hydroxyethyl)amino)-2-hydroxypropanesulfonic acid (pKa=7.6); 3-[N-Tris(hydroxymethyl)methylamino)-2-hydroxypropanesulfonic acid (pKa=7.6); Tris(hydroxymethyl) aminomethane (pKa=8.1); N-(2-hydroxyethyl)piperazine-N'-(2-hydroxypropanesulfonic acid) (pKa=7.8); Piperazine-N,N'-bis(2-hydroxypropanesulfonic acid) (pKa=7.8); N-(2-Hydroxyethyl)piperazine-N'-(3-propanesulfonic acid) (pKa=8.0); triethanolamined (pKa=7.8); N-Tris(hydroxymethyl)methylglycine (pKa=8.1); N,N-Bis(2-hydroxyethyl) glycine (pKa=8.3); N-Tris(hydroxymethyl)methyl-3-aminopropanesulfonic acid (pKa=8.4); 3-[(1,1-Dimethyl-2-hydroxyethyl)amino]2-hydroxypropanesulfonic acid (pKa=9.0); 2-(N-Cyclohexylamino)ethanesulfonic acid (pKa=9.3); 3-(Cyclohexylamino)-2-hydroxy-1-propanesulfonic acid (pKa=9.6); 2-Amino-2-methyl-1-propanol (pKa=9.7); and 2-(Cyclohexylamino)-1-propanesulfonic acid (pKa=10.4); amongst others. In some embodiments, the solute can include various acid salts such as sodium hydrogen sulfate, sodium hydrogen carbonate, sodium hydrogen sulfide, and various phosphatases. In some embodiments, the solute can include one or more low-temperature acid salts (such as potassium bitartrate, calcium phosphate, calcium citrate) or high-temperature acid salts (such as calcium aluminum phosphate).

Osmotic pH sensors as described herein can be disposed in various locations of the body, including within the coronary venous system. By way of example, in an embodiment, an osmotic pH sensor can be disposed on a lead, such as a coronary venous electrical stimulation lead, and positioned so that the osmotic pH sensor is within the coronary venous system.

Semi-Permeable Membranes

Embodiments of the invention can include a semi-permeable membrane. The term "semi-permeable membrane" as used herein shall refer to a membrane that is permeable to a solvent but impermeable to one or more solutes, such that the semi-permeable membrane can be used in the process of osmosis. The term "impermeable" as applied to an article, such as a membrane, shall refer to one that substantially blocks the passage of one or more compounds through its substance.

It will be appreciated that semi-permeable membranes can be constructed of many different types of materials. For example, semi-permeable membranes can include polymers such as cellulose, cellulose derivatives, polyacrylonitrile, polysulfone, polycarbonates, polyamides, polymethylmethacrylate (PMMA), polyethylenes, polytetrafluoroethylene (PTFE), and polysiloxanes. The specific choice of material can depend on factors such as desired tear strength, desired flexibility, and the like. In an embodiment, the semi-permeable membrane includes a biocompatible material.

In some embodiments, the semi-permeable membrane can be porous. The pores can have a diameter large enough to allow for the passage of water molecules but small enough to prevent the passage of various solutes found in bodily fluids.

The semi-permeable membrane can have a thickness that is sufficient to provide strength to prevent tearing under the conditions of use. In some embodiments, the semi-permeable membrane can be thin enough to maintain flexibility. In other embodiments, the semi-permeable membrane is substantially rigid. In some embodiments, the semi-permeable membrane is between about 1 nanometer and about 2 millimeters in thickness.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable osmotic heart monitoring system comprising: an osmotic pH sensor, the osmotic pH sensor configured to generate a signal corresponding to pH of a bodily fluid, the osmotic pH sensor comprising a wall member defining an enclosed volume, the wall member comprising a semi-permeable membrane; and a solution comprising a solvent and a solute, the solution disposed within the enclosed volume, the solute configured to change osmotic strength in a pH range of between about 7.3 and about 7.5, and the solute having a pKa of between about 6.0 and about 10.0; the semi-permeable membrane permeable to the solvent and impermeable to the solute; and a controller in communication with the osmotic pH sensor.

2. The implantable osmotic heart monitoring system of claim 1, the controller configured to generate a warning notification if the pH falls below a preselected threshold level.

3. The implantable osmotic heart monitoring system of claim 1, further comprising a lead comprising a lead body and a conductor disposed within the lead body, the conductor in electrical communication with the osmotic pH sensor and the controller.

4. The implantable osmotic heart monitoring system of claim 3, the osmotic pH sensor disposed on the lead body.

5. The implantable osmotic heart monitoring system of claim 4, the lead further comprising an electrode configured to interface with a target tissue.

6. The implantable osmotic heart monitoring system of claim 5, the controller further configured to generate electrical stimulation pulses to be delivered to the target tissue though the electrode.

7. The implantable osmotic heart monitoring system of claim 2, the preselected threshold level comprising a pH of 7.3.

8. The implantable osmotic heart monitoring system of claim 1, further comprising a first pressure sensor configured to sense the pressure within the enclosed volume.

9. The implantable osmotic heart monitoring system of claim 8, further comprising a second pressure sensor configured to sense the pressure outside of the enclosed volume.

10. The implantable osmotic heart monitoring system of claim 1, the semi-permeable membrane comprising a biocompatible material.

11. The implantable osmotic heart monitoring system of claim 1, the semi-permeable membrane having a thickness between about 1 nanometer and about 2 millimeters.

12. The implantable osmotic heart monitoring system of claim 1, the semi-permeable membrane comprising a polymer.

13. The implantable osmotic heart monitoring system of claim 12, the polymer comprising polytetrafluorethylene.

14. The implantable osmotic heart monitoring system of claim 1, the controller comprising a microprocessor.

15. The implantable osmotic heart monitoring system of claim 1, the solution disposed within the enclosed volume having a starting osmotic strength of between about 280 and 303 mOsm per kg.

16. The implantable osmotic heart monitoring system of claim 1, further including a housing and a header assembly, the osmotic pH sensor disposed on the housing.

17. The implantable osmotic heart monitoring system of claim 1, the solute comprising an acid salt.

18. The implantable osmotic heart monitoring system of claim 8, the first pressure sensor comprising an electrical pressure sensor.

19. The implantable osmotic heart monitoring system of claim 9, the second pressure sensor comprising an electrical pressure sensor.

20. The implantable osmotic heart monitoring system of claim 1, wherein the system is configured to modulate a minimum cardiac pacing rate based on the signal generated by the osmotic pH sensor.

* * * * *